(12) United States Patent
O'Hare et al.

(10) Patent No.: US 10,585,051 B2
(45) Date of Patent: Mar. 10, 2020

(54) X-RAY COMPUTED TOMOGRAPHY GAUGE

(71) Applicant: Hexagon Metrology, Inc., North Kingstown, RI (US)

(72) Inventors: Jonathan J. O'Hare, East Greenwich, RI (US); Zhanyu Ge, North Kingstown, RI (US)

(73) Assignee: Hexagon Metrology, Inc., North Kingstown, RI (US)

( * ) Notice: Subject to any disclaimer, the term of this patent is extended or adjusted under 35 U.S.C. 154(b) by 278 days.

(21) Appl. No.: 15/604,255

(22) Filed: May 24, 2017

(65) Prior Publication Data

US 2017/0343487 A1     Nov. 30, 2017

Related U.S. Application Data

(60) Provisional application No. 62/340,669, filed on May 24, 2016.

(51) Int. Cl.
*G01N 23/04* (2018.01)
*G01N 23/046* (2018.01)
*G01B 3/30* (2006.01)
*G01B 21/04* (2006.01)

(52) U.S. Cl.
CPC ............. *G01N 23/046* (2013.01); *G01B 3/30* (2013.01); *G01B 21/042* (2013.01); *G01N 2223/303* (2013.01)

(58) Field of Classification Search
None
See application file for complete search history.

(56) References Cited

U.S. PATENT DOCUMENTS

| | | |
|---|---|---|
| 5,442,674 A | 8/1995 | Picard et al. |
| 5,636,255 A | 6/1997 | Ellis |
| 5,793,835 A | 8/1998 | Blanck |
| 5,963,612 A | 10/1999 | Navab |
| 6,052,611 A | 4/2000 | Yanof et al. |

(Continued)

FOREIGN PATENT DOCUMENTS

| | | |
|---|---|---|
| DE | 10 2006 028 452 A1 | 12/2007 |
| EP | 1 760 457 A2 | 3/2007 |

(Continued)

OTHER PUBLICATIONS

Ahn et al., "Least-Squares Orthogonal Distances Fitting of Circle, Sphere, Ellipse, Hyperbola, and Parabola," Pattern Recognition, Elsevier, vol. 34, Issue 12, pp. 2283-2303, Dec. 2001.

(Continued)

*Primary Examiner* — Hoon K Song
(74) *Attorney, Agent, or Firm* — Nutter McClennen & Fish LLP (57) ABSTRACT

A method of making a gauge for verifying or calibrating an x-ray computed tomography device positions a first plurality of objects on a first substrate, and a second plurality of objects on a second substrate. The method also certifies the positions of both the first plurality of objects on the first substrate, and the second plurality of objects on the second substrate. After certifying both the first and second plurality of objects, the method couples the first substrate with the second substrate.

24 Claims, 8 Drawing Sheets

(56) References Cited

U.S. PATENT DOCUMENTS

| | | | |
|---|---|---|---|
| 6,364,529 B1* | 4/2002 | Dawson | A61B 6/583 378/18 |
| 7,569,829 B2 | 8/2009 | Chen et al. | |
| 7,594,753 B2* | 9/2009 | Main | A61N 5/1048 250/252.1 |
| 7,697,738 B2 | 4/2010 | Da Silva et al. | |
| 7,738,624 B2 | 6/2010 | Herold et al. | |
| 8,000,442 B2 | 8/2011 | Lachaine et al. | |
| 8,309,910 B2 | 11/2012 | Dutta et al. | |
| 8,764,290 B2 | 7/2014 | O'Hare et al. | |
| 8,777,485 B2 | 7/2014 | Holt | |
| 8,911,149 B2 | 12/2014 | O'Hare et al. | |
| 2003/0058999 A1 | 3/2003 | Mitschke et al. | |
| 2005/0094771 A1 | 5/2005 | Basu et al. | |
| 2005/0154548 A1 | 7/2005 | Basel et al. | |
| 2007/0122020 A1* | 5/2007 | Claus | A61B 6/583 382/131 |
| 2008/0075227 A1 | 3/2008 | Christoph et al. | |
| 2008/0093544 A1 | 4/2008 | Wang et al. | |
| 2013/0195239 A1 | 8/2013 | O'Hare et al. | |
| 2014/0153694 A1 | 6/2014 | Suppes et al. | |

FOREIGN PATENT DOCUMENTS

| | | |
|---|---|---|
| FR | 270 090 9 | 7/1994 |
| WO | WO 2012/150336 A1 | 11/2012 |
| WO | WO 2014/122218 A1 | 8/2014 |
| WO | WO 2015/199790 A1 | 12/2015 |
| WO | WO 2017/070442 A1 | 4/2017 |

OTHER PUBLICATIONS

Bartscher et al., "Achieving Traceability of Industrial Computed Tomography," Proceedings of ISMTII 2009, St. Petersburg, Russia, 6 pages, Jun. 29-Jul. 2, 2009.

Boas et al., "CT Artifacts: Causes and Reduction Techniques," Imaging Medicine, vol. 4, No. 2, pp. 229-240, Apr. 2012.

Dewulf et al., "Uncertainty Determination and Quantification for Dimensional Measurements with Industrial Computed Tomography," CIRP Annals—Manufacturing Technology, Elsevier, vol. 62, Issue 1, pp. 535-538, Apr. 2013.

ISO-GUM, "Evaluation of Measurement Data—Guide to the Expression of Uncertainty in Measurement," JCGM 100:2008—GUM 1995 with minor corrections, First Edition, 134 pages, 2008.

Johnston et al., "Geometric Calibration for a Dual Tube/Detector Micro-CT System," Medical Physics, vol. 35, Issue 5, pp. 1820-1829, May 2008.

Kiekens et al., "Uncertainty Determination for Dimensional Measurements with Computed Tomography," Conference on Industrial Computed Tomography, Austria, pp. 183-190, Sep. 19-21, 2012.

Konstantinidis, "Evaluation of Digital X-ray Detectors for Medical Imaging Applications, Electro-optical and X-ray Performance Evaluation of Novel Digital X-ray Detectors," Lambert Academic Publishing, 258 pages, 2012.

Kruth et al., "Computed Tomography for Dimensional Metrology," CIRP Annals—Manufacturing Technology, Elsevier, vol. 60, Issue 2, pp. 821-842, Jul. 13, 2011.

Lettenbauer et al., "Verification of the Accuracy of Computed Tomography," Quality Digest, 5 pages, Nov. 17, 2009.

Neugebauer et al., "A Geometrical Standard for Testing of X-Ray Computer Tomography," Technisches Messen, vol. 74, No. 11, pp. 565-571, Nov. 1, 2007 (in German).

Seifert et al., "Visualization of x-ray microtomography data for a human tooth atlas," Proceedings of the SPIE, Medical Imaging 2004: Visualization, Image-Guided Procedures and Display, vol. 5367, pp. 747-757, May 2004.

Späth, "Least Squares Fitting of Spheres and Ellipsoids Using Not Orthogonal Distances," Mathematical Communications, vol. 6, No. 1, pp. 89-96, Jun. 2001.

Weckenmann et al., "Assessment of Measurement Uncertainty Caused in the Preparation of Measurements Using Computed Tomography," XIX IMEKO World Congress—Fundamental and Applied Metrology, Lisbon, Portugal, pp. 1888-1892, Sep. 6-11, 2009.

Yang et al., "A Geometric Calibration Method for Cone Beam CT Systems," NIH Public Access Author Manuscript, Medical Physics, vol. 33, Issue 6, pp. 1695-1706, Jun. 2006.

International Searching Authority, Notification of Transmittal of the International Search Report and The Written Opinion of the International Searching Authority, or the Declaration, PCT/US2013/023602, dated May 2, 2013, 9 pages.

International Searching Authority, Notification of Transmittal of the International Search Report and The Written Opinion of the International Searching Authority, or the Declaration, PCT/US2015/025395, dated Aug. 5, 2015, 9 pages.

International Searching Authority, Notification of Transmittal of the International Search Report and The Written Opinion of the International Searching Authority, or the Declaration, PCT/US2016/058067, dated Jan. 12, 2017, 5 pages.

International Searching Authority, Notification of Transmittal of the International Search Report and The Written Opinion of the International Searching Authority, or the Declaration, PCT/US2017/034263, dated Jul. 14, 2017, 12 pages.

* cited by examiner

FIG.6B

# X-RAY COMPUTED TOMOGRAPHY GAUGE

PRIORITY

This patent application claims priority from provisional U.S. patent application No. 62/340,669, filed May 24, 2016, entitled, "X-RAY COMPUTED TOMOGRAPHY GAUGE," and naming Jonathan J. O'Hare and Zhanyu Ge as inventors, the disclosure of which is incorporated herein, in its entirety, by reference.

FIELD OF THE INVENTION

The invention generally relates to calibration devices and, more particularly, the invention relates to gauges for calibration of x-ray computed tomography devices/CT machines.

BACKGROUND OF THE INVENTION

Coordinate measuring machines (CMMs) are the gold standard for accurately measuring a wide variety of different types of work pieces. For example, CMMs can measure critical dimensions of aircraft engine components, surgical tools, and gun barrels. Precise and accurate measurements help ensure that their underlying systems, such as an aircraft in the case of aircraft components, operate as specified.

Inaccurate measurements can have catastrophic effects. Accordingly, to ensure that CMMs deliver accurate measurements, the CMM industry has developed well-defined accuracy verification standards, procedures, and gauging tools to calibrate and verify the underlying machines taking these measurements. To those ends, a CMM verification procedure typically requires hard gauges that are traceable for uncertainty calculations, and designed in such a way to ensure that they (i.e., the gauges) are dimensionally stable.

More recently, those in the art have begun using computed tomography (CT) systems as CMMs for coordinate metrology. Such CT systems known to the inventors can be subject to a variety of different calibration and verification standards.

SUMMARY OF VARIOUS EMBODIMENTS

In accordance with one embodiment of the invention, a method of making a gauge for calibrating an x-ray computed tomography device positions a first plurality of objects on a first substrate, and a second plurality of objects on a second substrate. The method also certifies the positions of both the first plurality of objects on the first substrate, and the second plurality of objects on the second substrate. After certifying both the first and second plurality of objects, the method couples the first substrate with the second substrate.

Among other ways, the method may certify the first plurality of objects using a tactile probe of a coordinate measuring machine to confirm the positions of the first plurality of objects. The same process may be used to certify the second plurality of objects. The first and second substrates preferably are substantially planar. In that case, the method may orient the first substrate to be substantially orthogonal to the second substrate when coupled.

Since the gauge is expected to be used to calibrate or verify a CT measurement device, the first plurality of objects includes at least three objects in a substantially straight line. To improve measurement versatility, the objects preferably are oriented and positioned to comply with at least two measurement standards. The first plurality of objects may be adhered to the first substrate, at the noted precise locations, in a number of manners, such as with an epoxy or UV activated glue.

To effectively perform their respective functions, the first and second pluralities of objects are visible to x-rays and each have an object attenuation value to x-rays. In various embodiments, the objects may include precision ground or lapped objects (e.g., ruby or sapphire spheres).

In a manner similar to the objects, the first and second substrates each also have a base attenuation value to x-rays. To mitigate x-ray interference from the substrates, the object attenuation values preferably each are greater than each of the base attenuation values.

In accordance with another embodiment, a method of determining error of an x-ray computed tomography device positions a gauge within an x-ray computed tomography device. The gauge has a first plurality of certified objects on a first substrate and a second plurality of certified objects on a second substrate. The first and second substrates are coupled and diverging. Next, the method images the gauge to form a three-dimensional model representing the gauge. After forming the model, the method locates a plurality of the first objects in the three-dimensional model, and measures between the plurality of located first objects to produce a first measurement. The method then compares the first measurement against a first prescribed measurement value to produce a difference value. Specifically, the difference value indicates a degree of a first error of the x-ray computed tomography device. This error could be zero (i.e., no error) or non-zero.

In accordance with other embodiments of the invention, a gauge for calibrating or verifying an x-ray computed tomography device has first and second planar substrates. The first substantially planar substrate has at least three first objects forming a substantially straight line. In a similar manner, the second substantially planar substrate has at least three second objects that also forming a substantially straight line. The first and second substrates are coupled together (e.g., they are either removably coupled or permanently coupled) and diverge (i.e., they are not parallel).

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

Illustrative embodiments produce a versatile, multi-standard gauge for calibrating and verifying an x-ray computed tomography device. To act as measurement waypoints, the gauge has a plurality of objects that permit a user to calibrate and verify the tomography device using any one of a plurality of different standards. Among others, those standards may include VDI/VDE (Association of German Engineers), ISO (International Organization for Standardization), ASME (American Society of Mechanical Engineers), and ASNT (American Society for Nondestructive Testing) standards. To that end, illustrative embodiments position objects on two separate substrates, certify both substrates separately (e.g., using a CMM device), and then couple the two substrates together to form the gauge. Details of illustrative embodiments are discussed below.

Figure 1A:
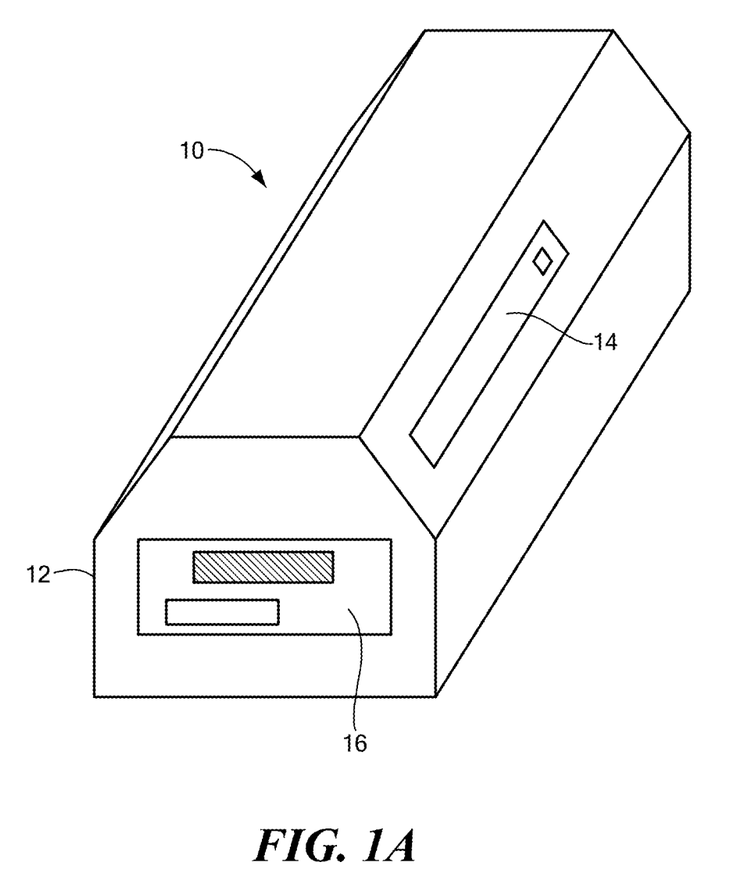
FIG. 1A schematically shows an x-ray computed tomography device that may use illustrative embodiments of the invention.
Figure 1B:
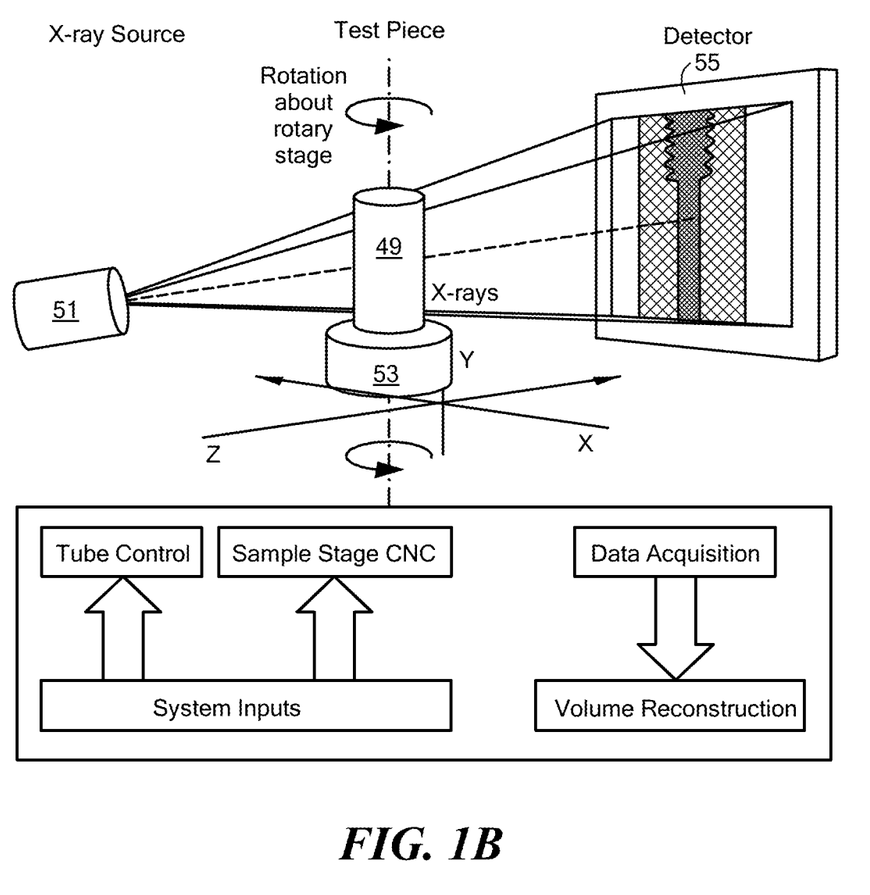
FIG. 1B schematically shows internal components of the device of FIG. 1A.

FIGS. 1A and 1B respectively show exterior and interior views of an x-ray machine/computer tomography device 10 that may use a calibration gauge configured in accordance with illustrative embodiments. It should be noted that although this discussion primarily relates to calibration, principles of various embodiments apply to verification of the accuracy of x-ray computed tomography machines 10. Specifically, some embodiments may use the gauge to verify the accuracy of the x-ray computed tomography machine 10 to determine an error in its measurements/settings. In response, the x-ray computed tomography machine 10 may be calibrated (e.g., using the noted gauge or a different gauge) to correct detected inaccuracies. Accordingly, discussion of calibration is not intended to limit all embodiments of the invention.

Among other things, the x-ray computed tomography 10 may be a computed tomography system (a/k/a "CT system" or a CT machine) that produces a three dimensional model of a work piece within its interior (referred to as a "work piece reconstruction"). To those ends, the x-ray computed tomography machine 10 has a housing 12 forming an interior chamber for containing, among other things (see FIG. 1B):

1) a work piece 49 to be measured,
2) an x-ray gun 51 for generating x-rays,
3) a rotary stage 53 (aka a "rotary table") for rotating the work piece 49, and
4) a detector 55 for detecting the image of the work piece after it is imaged by the x-ray gun 51.

An access door 14, which may be made from a transparent material, provides access to the interior for adding and removing work pieces. For example, the work piece may be a cardiovascular stent commonly used in coronary angioplasty procedures. A control panel 16 on the side of the machine 10 acts as the control interface for an operator.

To produce a 3D model of the work piece (the "reconstruction"), the CT system moves the work piece relative to the x-ray guns 51. For example, the CT system may rotate the work piece a full 360 degrees on the rotary stage 53, and take multiple x-ray images (known in the art as "projections" or "projection angles") of the work piece during rotation. During and/or after rotating the work piece, a model building module (e.g., post-processing software executing on a local microprocessor or microcontroller) converts the data of all the projections into a 3D model of the work piece-the noted reconstruction. It is this 3D model—which may be a software model—that may be measured to confirm the work piece's dimensional accuracy. Thus, if the work piece is a small medical device, such as a cardiovascular stent, then measurement software may precisely measure selected features of the stent, such as its radius, wall thickness, etc.

If the CT system is not properly calibrated, however, then these work piece measurements likely will be inaccurate. Accordingly, the operator or other person should calibrate the CT system prior to use. Illustrative embodiments thus use a gauge to confirm/calibrate system accuracy (as well as verify measurements). This gauge preferably is configured so that the user may calibrate the system using any one of a plurality of different calibration and measurement standards.

Figure 2:
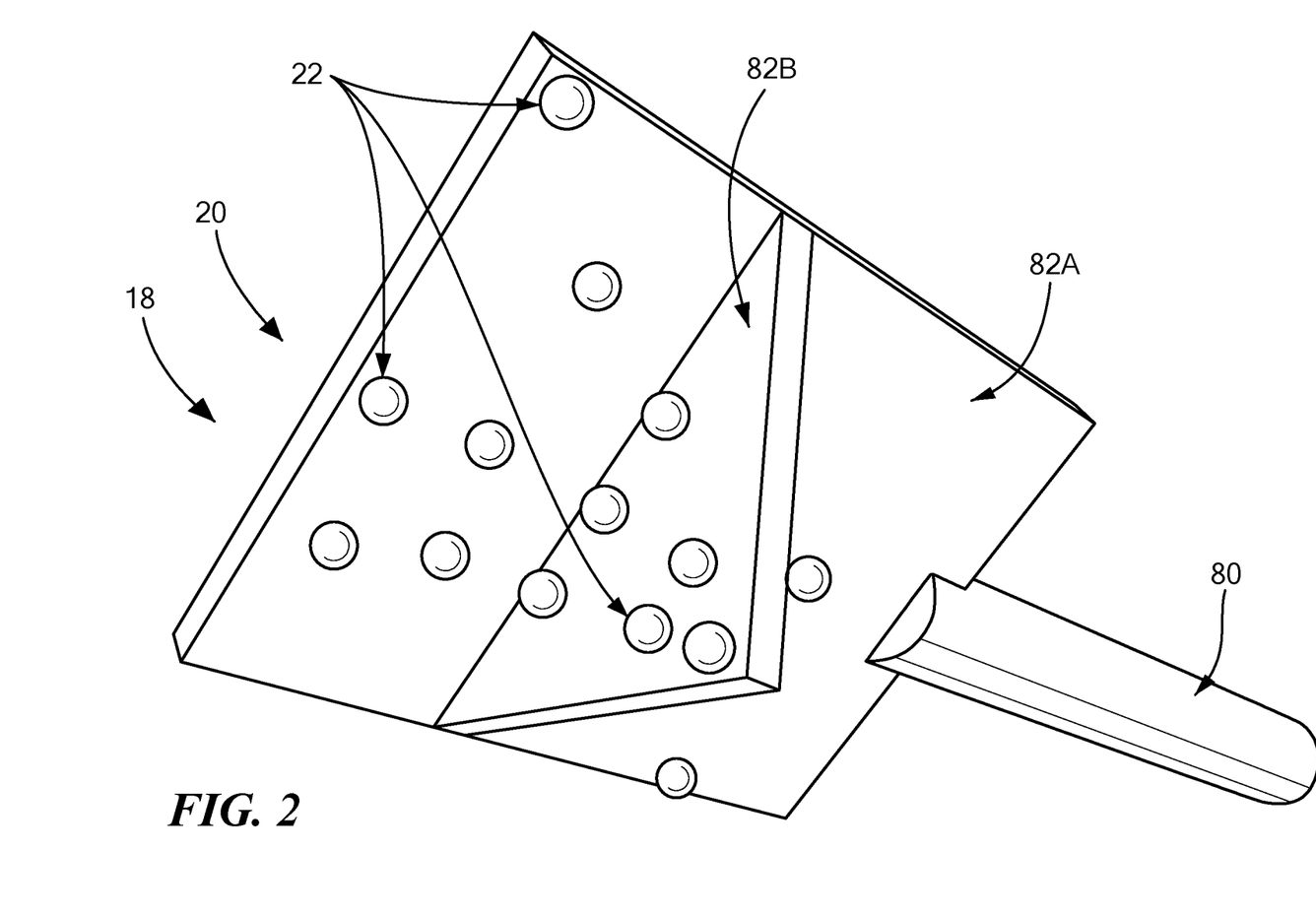
FIG. 2 schematically shows an x-ray calibration and verification gauge configured in accordance with illustrative embodiments of the invention.

To those ends, FIG. 2 schematically shows an x-ray calibration and verification gauge configured in accordance with illustrative embodiments of the invention. The gauge 18 has a multi-planar base 20 that supports a plurality of discrete objects 22 that act as waypoints/fiduciary points in the calibration process. A post 80 or other member may couple with the base 20 to support the gauge 18 when in use (discussed below).

The base 20 preferably includes a first, substantially planar substrate or base member (referred to as "first substrate 82A") coupled with a second, substantially planar substrate or base member (referred to as "second substrate 82B"). When used generally, the term "substrate" is identified by reference number "82." In the example shown in FIGS. 2 and 4-5, each of these two substrates 82A and 82B is generally rectangular and flat. Other embodiments, however, may have non-rectangular substrates. For example, one of the substrates 82A or 82B may form a triangle, while the other substrate 82A or 82B may form a hexagon. Alternative embodiments also may use one or more substrates that have some contour or surface topology. The relative sizes, geometries, and dimensions of the substrates 82A and 82B thus may be the same, or they may be different.

The objects 22 are precisely positioned on the substrates 82A and 82B to comply with at least two different calibration standards, such as those discussed above (e.g., ISO, ASME, or ASNT standards). Current standards known to the inventors typically require measurement between or along at least three objects 22 (e.g., spheres) that form a straight line. For example, many measurement device calibration standards require measurement in seven different directions, such as along prescribed X, Y, and Z axes, and in four directions generally orthogonal to those axes (e.g., diagonal directions). To that end, to comply with currently known standards, each substrate 82A and 82B has one or more sets of at least three spaced apart objects 22 (e.g., spheres) positioned in a straight line. For example, the substrate 82A of FIG. 2 has ten spheres 22 on the same side that form seven straight lines. Accordingly, the sets of three spheres (also identified by reference number "22") may have common spheres 22, or all have different spheres 22. For example, first second and third spheres on the first substrate 82A may form a first line, while the first, third and a fourth sphere may form another straight line on the same substrate 82A.

As discussed below, during intended use, a user calibrates the CT system by measuring between spheres 22 on the same substrate 82A or 82B—not between spheres 22 on different substrates 82A and 82B. For example, a user may measure between three spheres 22 on the first substrate 82A, or measure between three spheres 22 on the second substrate 82B. Alternative embodiments, however, may measure between spheres 22 on different substrates 82A and 82B.

Although current standards are contemplated, those skilled in the art could position the objects 22 in different orientations as standards evolve. Accordingly, discussion of requirements of currently known standards is not intended to limit various embodiments of the invention.

The objects 22 may include a plurality of spheres 22 that are ground or lapped to have very precise qualities (precise symmetry, shape, size, volumes, centers, geometry, etc.). In illustrative embodiments, the spheres 22 are certified by some reliable and well-known third party to have certain measurement qualities. The spheres 22 are independent structures—they are not integral to or even connected to each other. Instead, the spheres 22 are spaced out across the base 20 in a prescribed manner (e.g., in contact with other spheres 22 or spaced from other spheres 22). As discussed in greater details below, illustrative embodiments position plural spheres 22 so that their centers together form a straight line.

The spheres 22 preferably are formed to have a very fine precision. For example, the spheres 22 have a substantially spherical form with a precision to at least 0.01 millimeters. Specifically, as used herein, a precision of at least 0.01 millimeters may have an even finer precision, such as 0.001 millimeters, 0.005 millimeters, 0.0001 millimeter, 0.00001 millimeters, etc. As another example, the spheres 22 may have a diameter of 10.0001 millimeters, within some known tolerance, such as 0.00005 millimeters. All spheres 22 of the same gauge 18 may be the same size, or different. In either case, the diameters of the spheres 22 are known to the precision noted. Accordingly, illustrative embodiments can detect a variance of the reading by the CT machine 10 by an amount on the order of the precision of the sphere 22—down to the micrometer or nanometer level.

To calibrate the CT system, a noted calibration module (discussed below with regard to FIGS. 6A and 6B and identified by reference number "100") measures the distance between some identifiable regions of the objects 22. For example, in the sphere implementation, as suggested above, the calibration module 100 may measure between the centers of the one or more of the spheres 22. If the object 22 was not in the form of a sphere (e.g., in the form of a protrusion, cube, cylinder, irregular shape, etc.), then the identifiable region could be the center or some other area, such as an end, a discontinuity, a corner, the intersection of two portions, etc. Even if the objects 22 are geometrically shaped as spheres, the identifiable portion could be an outside region.

Indeed, it is critical for the spheres 22 to be visible on the x-ray images. To that end, the spheres 22 preferably are formed from a material having a higher attenuation to x-rays than the attenuation produced by the base 20. For example, the spheres 22 may be formed from ruby, sapphire, or other material for the purpose of providing low thermal expansion and x-ray attenuation near the middle of the CT system's range of intensity values. In contrast, the base 20 may be formed primarily from a ceramic material (e.g., boron nitride) with a high stiffness and a low thermal expansion, but with an x-ray attenuation that is relatively low compared to that of the spheres 22. This differential in attenuations should be selected to provide good contrast and a clear separation between the surfaces of interest (i.e., the spheres 22) and the base 20. Those in the art should understand that the base 20 may be formed from another material having similar properties. Moreover, in illustrative embodiments, the coefficient of thermal expansion of the spheres 22 and base 20 is as low as possible, such as no greater than that for steel.

Figure 3:
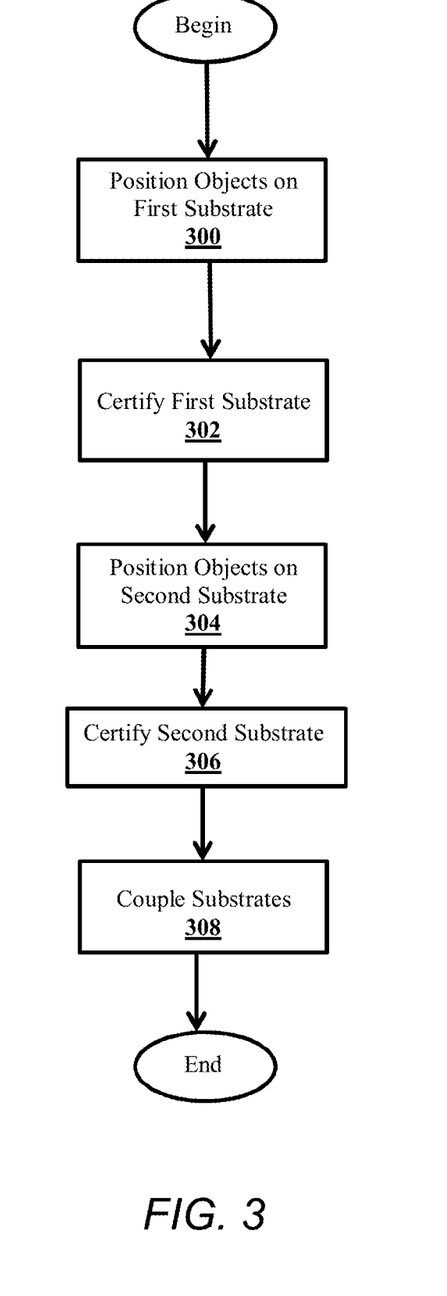
FIG. 3 shows a process of forming the x-ray calibration and verification gauge of FIG. 2 and accordance with illustrative embodiments of the invention.

FIG. 3 shows a process for forming the gauge 18 in accordance with illustrative embodiments of the invention. It should be noted that this process is simplified from a longer process that normally would be used to form the gauge 18. Accordingly, the process of forming the gauge 18 may have many additional steps that those skilled in the art likely would use. In addition, some of the steps may be performed in a different order than that shown, or at the same time. Those skilled in the art therefore can modify the process as appropriate. Moreover, as noted above and below, many of the materials and structures noted are but examples of a wide variety of different materials and structures that may be used. Those skilled in the art can select the appropriate materials and structures depending upon the application and other constraints. Accordingly, discussion of specific materials and structures is not intended to limit all embodiments.

The process of FIG. 3 begins at step 300, which positions objects 22 on the first substrate 82A. As noted above, these objects 22 preferably are precisely positioned to pre-specified locations to comply with at least one standard. Those skilled in the art can use any of a wide variety of techniques for positioning or securing the objects 22 onto the respective substrates 82A and 82B. For example, illustrative embodiments may secure the spheres 22 to the first substrate 82A using an epoxy or ultraviolet actuated adhesive.

After positioning the objects 22 on the first substrate 82A, the method certifies the first substrate 82A. Specifically, step 302 precisely measures distances between the objects 22 to ensure that they are a prescribed distance apart. To that end, illustrative embodiments preferably use a reliable, precise measurement device, such as a coordinate measuring machine ("CMM"). For example, the coordinate measuring machine may measure the distances using a tactile probe or a noncontact probe.

Steps 304 and 306 respectively complete the same steps as steps 300 and 302 for the second substrate 82B in a similar manner. Accordingly, in a manner similar to the objects 22 on the first substrate 82A, the objects 22 on the second substrate 82B are precisely positioned to comply with at least one standard. That standard could be the same standard as that on the first substrate 82A, or a different standard. For example, the first substrate 82A may be arranged in accordance with a first standard, while the second substrate 82B may be arranged in accordance with a second, different standard. Alternatively, both the first and second substrates 82A and 82B may be arranged so that both are arranged and required to calibrate/verify using a single standard. Some embodiments, however, may position the objects 22 to comply with two standards on one substrate 82A or 82B, and no standard on another substrate 82A or 82B.

Figure 4:
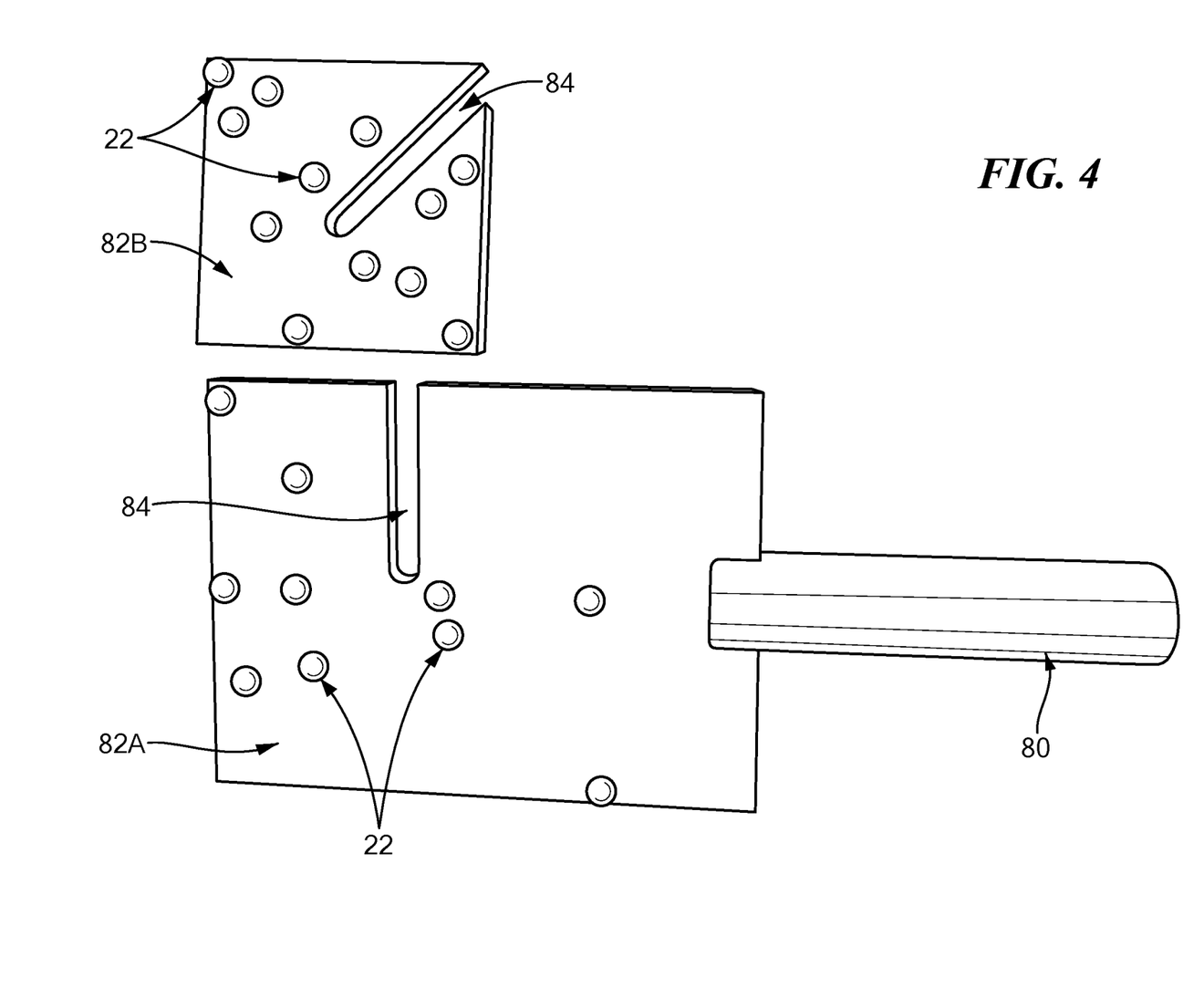
FIG. 4 schematically shows two planar substrates of the x-ray calibration and verification gauge of FIG. 2 before step 308 couples them together.

FIG. 4 schematically shows the first and second substrates 82A and 82B after completing step 306. As substantially planar members, a tactile probe or other measurement mechanism from a CMM can more easily access the objects 22. In other words, when the substrates 82A and 82B are separated apart, as shown in FIG. 4, the CMM can more easily measure the distances between the objects 22. Moreover, unlike prior art gauges known to the inventors, fabricating the gauge 18 using substantially planar substrates 82A and 82B is generally a simpler, faster, and less costly process.

It should be noted that the figures show at least one of the substrates 82A or 82B as having the above noted post 80 to support the gauge during use. Some embodiments may have more than one post 80, posts 80 on each substrate 82A and 82B, or no posts 80. Other embodiments may use another type of support member. As such, discussion of the post 80 is but one example and not intended to limit such embodiments.

Figure 5:
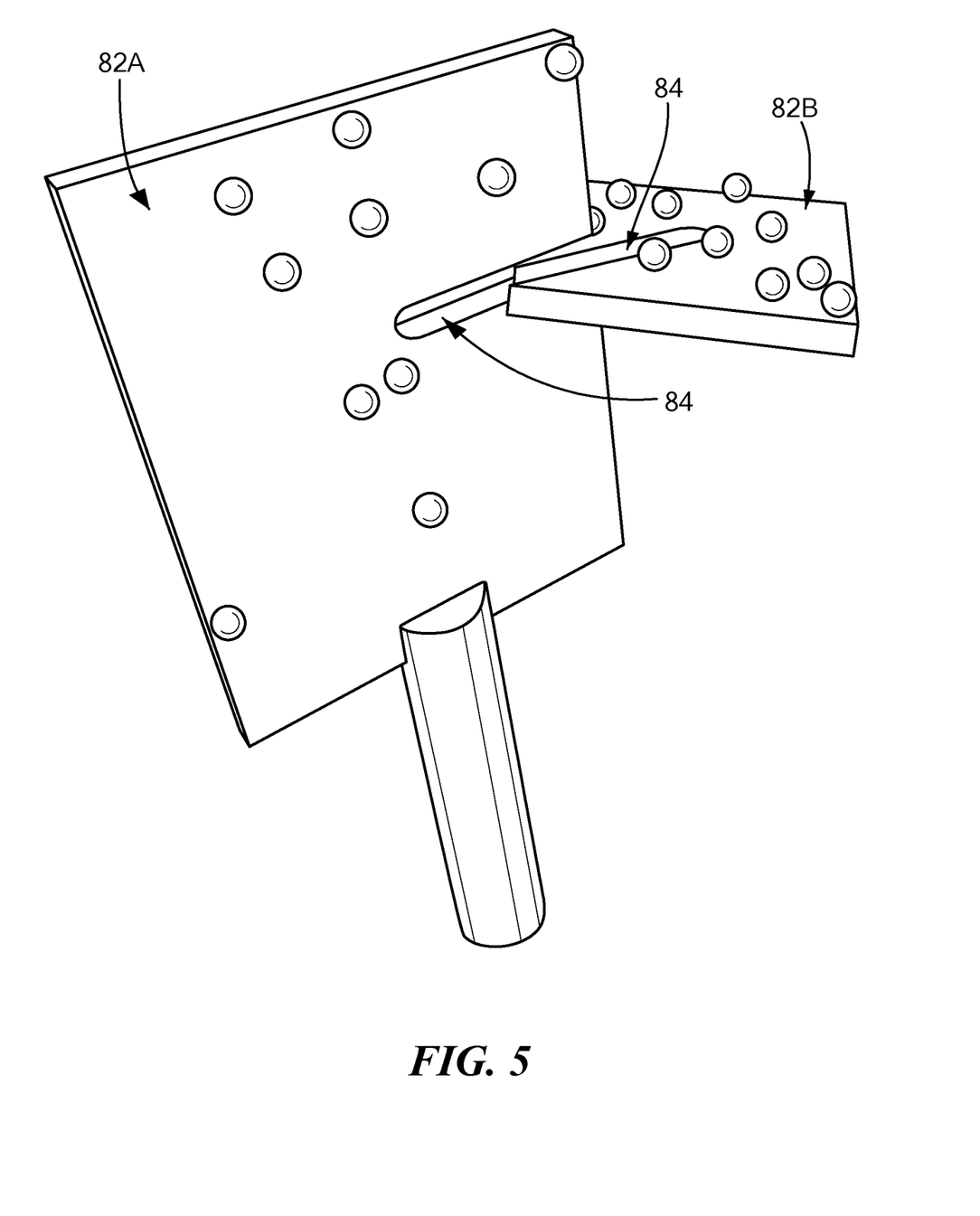
FIG. 5 schematically shows the 2 planar substrates of FIG. 4 as step 308 couples them together.

The process concludes at step 308, which couples the first substrate 82A with the second substrate 82B. For example, FIG. 5 schematically shows the two substrates 82A and 82B as they are being coupled. As shown in this embodiment, each of the substrates 82A/82B has a complimentary notch 84 that couples with the notch 84 of the other substrate 82A/82B to make a secure substrate-to-substrate connection. Adhesive, snap fit, frictional fit, or other coupling techniques may secure the two substrates 82A and 82B together. In illustrative embodiments, absent the application of unintended and/or substantial force (e.g., using a saw or forcibly breaking the two apart, such as by breaking a bonding between the two), the two substrates 82A and 82B are not separable. In other embodiments, however, the two substrates 82A and 82B are removably connected/coupled—they can be separated and put together again with minimal effort (e.g., using a snap-fit mechanism or simple frictional connection).

Removably coupled substrates 82 provide a number of benefits when compared to non-removably coupled substrates 82. Among others, they are more flexible in their use. For example, one could use just one substrate 82A or 82B to run a quick scan without the need for the objects 22 on the other substrate 82A or 82B. Another benefit is ease of transport. Specifically, shipping or transporting the two substrates 82A and 82B as separated pieces should require less volume for shipping and reduce the likelihood that the gauge 18 will break.

As shown in FIG. 2, the first substrate 82A may be coupled to the second substrate 82B so that the two substrates 82A and 82B are substantially orthogonal to each other. Other embodiments, however, may couple the two substrates 82A and 82B to each other so that they form other angles, such as 60 degrees or 45 degrees.

To support even more standards, some embodiments may have more than two substrates 82A and 82B. For example, the gauge 18 may have three substrates 82 positioned to form a common center and forming sixty-degree angles with each adjacent substrate 82. As another example, the gauge 18 may position third and/or fourth substrates 82 that only contact one other substrate 82. Those skilled in the art can select the appropriate configuration.

Some embodiments form a kit with a plurality of substrates 82. Each substrate preferably is removably connectable with another substrate (e.g., the substrate 82A) and may represent a different calibration standard. Accordingly, a user may select the appropriate substrate 82 based on the calibration standard desired. The gauge 18 may have a base substrate 82 that has objects 22 covering common measurements of two or more different standards, and a second set of substrates 82 with objects 22 covering measurements that differ across those two or more same standards.

Those skilled in the art may position the substrates 82A and 82B together so that they are not necessarily symmetrical. FIG. 2, for example, schematically shows a generally symmetrical arrangement of the substrates 82A and 82B. Alternatively, some embodiments may position the substrates 82A and 82B in an asymmetrical manner, such as by coupling the second substrate 82B to or near one edge of the first substrate 82A.

Figure 6A:
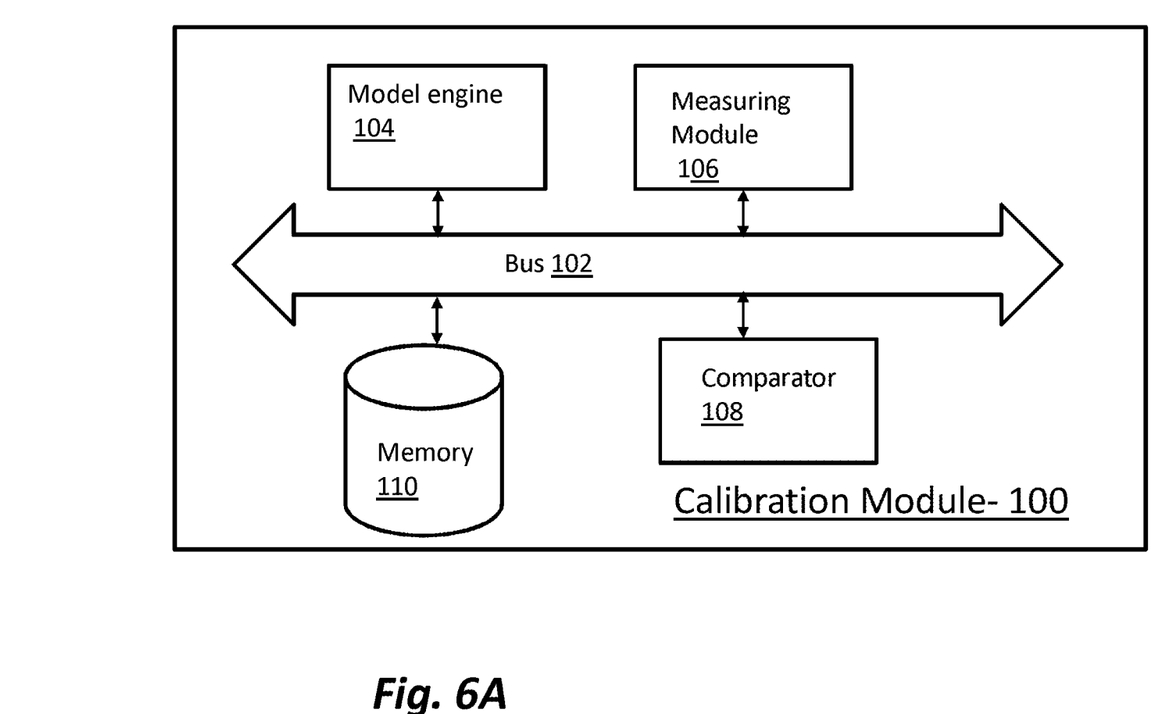
FIG. 6A schematically shows a calibration module (or a verification module) configured in accordance with illustrative embodiments of the invention.

As noted above, the calibration module 100 has logic to measure and determine the error for calibration and/or verification purposes. To that end, FIG. 6A schematically shows the calibration module 100 configured in accordance with illustrative embodiments of the invention. Each of these components is operatively connected by any conventional interconnect mechanism. FIG. 6A simply shows a bus 102 communicating each the components. Those skilled in the art should understand that this generalized representation can be modified to include other conventional direct or indirect connections. Accordingly, discussion of a bus 102 is not intended to limit various embodiments.

Indeed, it should be noted that FIG. 6A only schematically shows each of these components. Those skilled in the art should understand that each of these components can be implemented in a variety of conventional manners, such as by using hardware, software, or a combination of hardware and software, across one or more other functional components. For example, a model engine (discussed below and identified by reference number "104") may be implemented using a plurality of microprocessors executing firmware. As another example, the model engine 104 may be implemented using one or more application specific integrated circuits (i.e., "ASICs") and related software, or a combination of ASICs, discrete electronic components (e.g., transistors), and microprocessors. Accordingly, the representation of the model engine 104 and other components in a single box of FIG. 6A is for simplicity purposes only. In fact, in some embodiments, the model engine 104 of FIG. 6A is distributed across a plurality of different machines—not necessarily within the same housing or chassis.

It should be reiterated that the representation of FIG. 6A is a significantly simplified representation of an actual calibration module Those skilled in the art should understand that such a device may have many other physical and functional components, such as central processing units, interfaces, and short-term memory. Accordingly, this discussion is in no way intended to suggest that FIG. 6A represents all of the elements of the calibration module 100.

As shown, the calibration module 100 includes the noted model engine 104, which converts a plurality of x-ray images into the above noted reconstruction, and a measuring module 106 for measuring between objects 22 on the specific substrates 82A and/or 82B. The calibration module 100 also has memory 110 for storing actual, preferably certified distances between specific objects 22, and a comparator 108 for comparing measured distances against known distances in the memory 110. In illustrative embodiments, the actual distance values are stored in a database within the memory 110. The memory 110 may store other data, such as the logical representation of a 3D model of the gauge 18, and measurement values between objects 22 on the gauge 18.

Figure 6B:
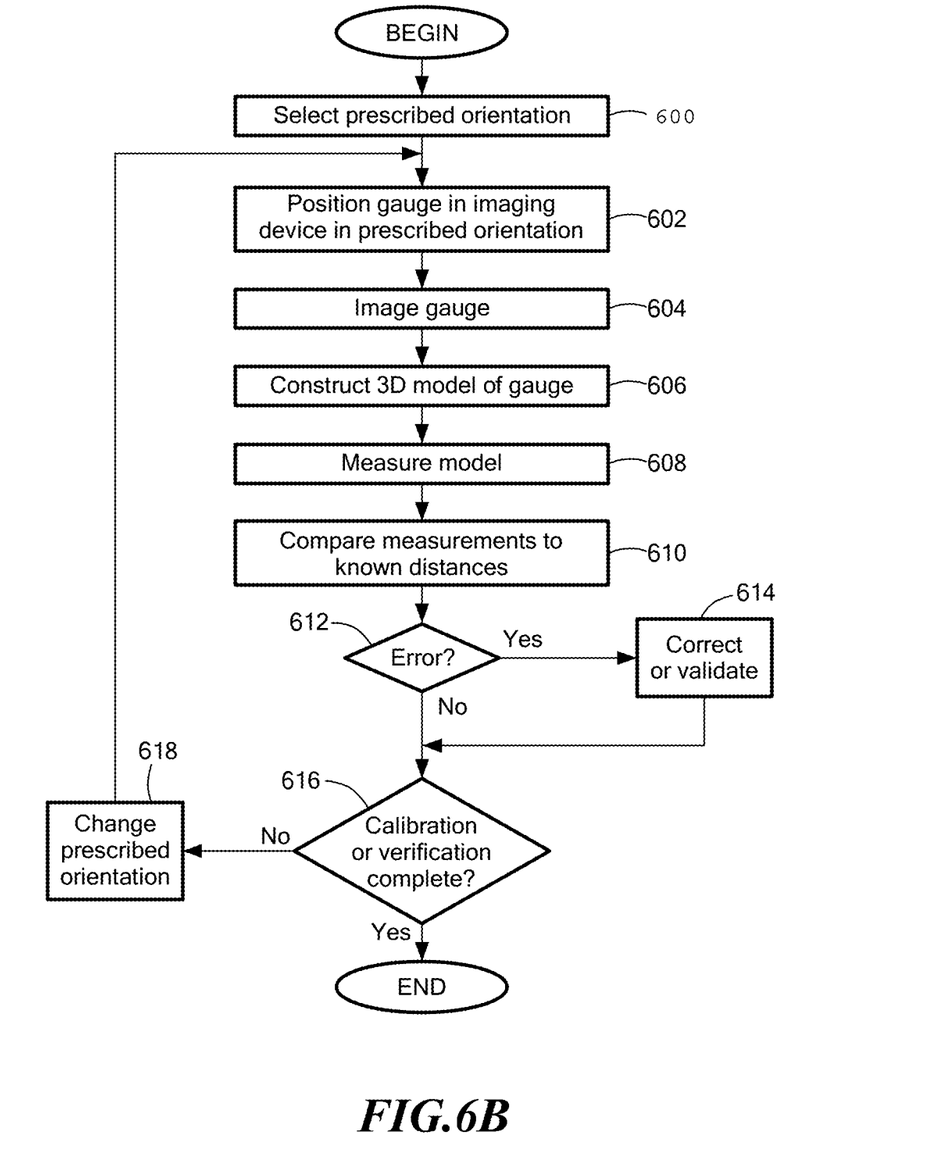
FIG. 6B shows a process of using the gauge of FIG. 2 in the x-ray computed tomography device of FIG. 1.

FIG. 6B shows a process of using the gauge 18 and the calibration module 100 of FIG. 6A in accordance with one embodiment of the invention. In a manner similar to the process of FIG. 3, this process may include steps that are not discussed. Accordingly, the process of using the gauge 18 and calibration module 100 may have many additional steps that those skilled in the art may use. In addition, some of the steps may be performed in a different order than that shown, or at the same time. Those skilled in the art therefore can modify the process as appropriate.

The process begins at step 600 by selecting a prescribed orientation for the gauge 18 within the x-ray computed tomography machine 10. A user may make this selection based on the standard intended to be used to calibrate and/or verify the x-ray computed tomography machine 10. Next, the process/user/robot physically positions the gauge 18 within the x-ray computed tomography machine 10 in the prescribed orientation (step 602). For example, the process may set the post 80 on the rotary table 53, or set the post 80 in a holding device, such as a clamp (not shown). Some embodiments without a post 80 may simply position the two substrates 82A and 82B (forming the base 20) directly on the rotary table 53.

After it is positioned within the CT machine 10, the gauge 18 may be imaged (step 604). To that end, the rotary table 53 preferably rotates the gauge 18 a full 360 degrees (some embodiments may not rotate the full 360 degrees). During this time, the x-ray computed tomography machine 10 generates sequenced images/projections of the gauge 18 for subsequent processing.

After the x-ray computed tomography machine 10 finishes imaging the gauge 18, the model engine 104 constructs a three-dimensional model ("3D model") representing the gauge 18 (step 606). To that end, the model engine 104 uses the data from the successive images to construct the 3D model—a gauge reconstruction, which can be stored in the memory 110 of the calibration module 100. Although not necessary, a rendering device (e.g., rendering software-not shown) may render the 3D model, and then rotate or otherwise move the ultimate 3D model for a viewer, thus showing the details of the gauge 18.

Next, at step 608, the measuring module 106 measures the 3D model objects 22 to determine if the reconstruction is dimensionally accurate. To that end, using one or more of the prescribed standards, the measuring module 106 measures between preselected points within the gauge reconstruction. For example, the measuring module 106 may measure between the centroids of prescribed spheres 22. This step thus produces a plurality of values for verification in subsequent steps.

Specifically, the actual distance between the prespecified points is known—in a database in the memory 110; in preferred embodiments, those distances are certified (e.g., steps 302 and 306 of FIG. 3). For example, the known distance between the centers of two spheres 22 can be 10.0001 millimeters. The known distance between the centers of two other spheres 22 could be 20.0002 millimeters.

Accordingly, at step 610, the comparator 108 compares those different measured distances against the known distances and determines if there are errors (step 612). This difference is the calibration error of the machine 10. Using the example above, if the measured distance between the first two spheres 22 (known distance 10.0001 millimeters) is 10.0004 millimeters, then the CT machine 10 has an error of 0.0003 millimeters and thus, should be appropriated adjusted.

Accordingly, if the calibration module 100 detects errors beyond some preset limits or tolerances (e.g., detecting this exemplary 0.0003 millimeter error), then step 614 corrects the error by refining the initial calibration settings of the CT machine 10. Those skilled in the art may re-calibrate or initially calibrate the CT machine 10 in a conventional manner. After correcting the errors by step 614, or if there are no errors from step 612, the process continues to step 616 to determine if calibration or verification is complete. If it is complete, then the process ends. If not complete, then the process may change the prescribed orientation of the gauge 18. For example, the prescribed orientation can be moved to be rotated and/or at an angle to the initial prescribed orientation. By doing this, the operator can test various different axes within the CT machine 10. Other embodiments, however may calibrate and/or verify with just a single scan and orientation of the gauge 18. That single scan can be used to take a plurality of different measurements. That total number of measurements may be equal to the total number of measurements required by a given standard (e.g., seven measurements).

Accordingly, illustrative embodiments of the gauge 18 are move easily manufacturable and transportable. In addition, when using removably connectable substrates 82, only a single substrate 82 may be used for a quick scan.

Although the above discussion discloses various exemplary embodiments of the invention, it should be apparent that those skilled in the art can make various modifications that will achieve some of the advantages of the invention without departing from the true scope of the invention.

What is claimed is:

1. A method of making a gauge for calibrating or verifying an x-ray computed tomography device, the method comprising:
   positioning a first plurality of objects on a first substrate;
   certifying the positions of the first plurality of objects on the first substrate;
   positioning a second plurality of objects on a second substrate;
   certifying the positions of the second plurality of objects on the second substrate;
   coupling the first substrate with the second substrate after certifying both the first and second plurality of objects,
   wherein the first plurality of objects and the second plurality of objects are formed from a material having an attenuation to x-rays such that the first plurality of objects and the second plurality of objects are visible on x-ray images.

2. The method as defined by claim 1 wherein certifying the first plurality of objects comprises using a tactile probe of a coordinate measuring machine to confirm the positions of the first plurality of objects.

3. The method as defined by claim 1 wherein the first substrate is substantially planar and the second substrate is substantially planar, further wherein coupling comprises orienting the first substrate to be substantially orthogonal to the second substrate when coupled.

4. The method as defined by claim 1 wherein the first plurality of objects includes at least three objects in a substantially straight line.

5. The method as defined by claim 1 wherein positioning the first plurality of objects comprises securing the first plurality of objects to the first substrate using an epoxy or ultraviolet activated glue.

6. The method as defined by claim 1 wherein the first plurality of objects and second plurality of objects are visible to x-rays and each having an object attenuation value to x-rays, the first and second substrates each having a base attenuation value to x-rays, the object attenuation values each being greater than the base attenuation values.

7. The method as defined by claim 1 wherein the objects are oriented and positioned to comply with at least two measurement standards.

8. The method as defined by claim 1 wherein the first plurality of objects comprise precision ground or lapped objects.

9. The method as defined by claim 1 wherein the first plurality of objects are substantially spherically shaped.

10. The method as defined by claim 1 wherein coupling comprises removably coupling the first substrate with the second substrate.

11. A gauge for calibrating or verifying an x-ray computed tomography device, the gauge comprising:
    a first substantially planar substrate having at least three first objects forming a substantially straight line;

a second substantially planar substrate having at least three second objects forming a substantially straight line, the first and second substrates being coupled and diverging wherein the at least three first objects and the at least three second objects are formed from a material having an attenuation to x-rays such that the first plurality of objects and the second plurality of objects are visible on x-ray images.

12. The gauge as defined by claim 11 wherein the first and second substrates are substantially orthogonal to each other.

13. The gauge as defined by claim 11 wherein the first and second substrates are removably connected.

14. The gauge as defined by claim 11 wherein the first substrate has a fourth object that forms a straight line with two of the at least three first objects.

15. The gauge as defined by claim 14 wherein the second substrate has a fifth object that forms a straight line with two of the at least three second objects.

16. The gauge as defined by claim 14 wherein the first substrate forms a first notch and the second substrate forms a second notch, the first substrate removably coupling to the second substrate with the first and second notches.

17. The gauge as defined by claim 11 wherein each of the objects are substantially spherically shaped.

18. A method of determining error of an x-ray computed tomography device, the method comprising:

positioning a gauge within an x-ray computed tomography device, the gauge comprising a first plurality of objects on a first substrate and a second plurality of objects on a second substrate, the first and second substrates being coupled and diverging;

imaging the gauge;

forming a three-dimensional model representing the gauge;

locating a plurality of the first objects in the three-dimensional model;

measuring between the plurality of located first objects to produce a first measurement; and comparing the first measurement against a first prescribed measurement value to produce a difference value, the difference value indicating a degree of a first error of the x-ray computed tomography device.

19. The method as defined by claim 18 further comprising:

locating a plurality of the second objects in the three-dimensional model;

measuring between the plurality of located second objects produce a second measurement; and comparing the second measurement against a second prescribed measurement value to produce a difference value, the difference value indicating a degree of a second error of the x-ray computed tomography device.

20. The method as defined by claim 18 further comprising:

removably coupling the first substrate with the second substrate before measuring; and uncoupling the first substrate and the second substrate after comparing.

21. The method as defined by claim 18 wherein the degree of the first error includes a non-zero error.

22. The method as defined by claim 18 wherein the first substrate is substantially planar and the second substrate is substantially planar.

23. The method as defined by claim 18 further comprising:

measuring, using the three-dimensional model, a first given number of times between the first plurality of objects on the first substrate;

measuring, using the three-dimensional model, a second given number of times between the second plurality of objects on the second substrate, the sum of the first and second given number of times equaling the total number of measurements for a given x-ray standard.

24. The method as defined by claim 18 wherein the first and second plurality of objects are certified.

* * * * *

UNITED STATES PATENT AND TRADEMARK OFFICE
CERTIFICATE OF CORRECTION

PATENT NO. : 10,585,051 B2
APPLICATION NO. : 15/604255
DATED : March 10, 2020
INVENTOR(S) : Jonathan J. O'Hare et al.

Page 1 of 1

It is certified that error appears in the above-identified patent and that said Letters Patent is hereby corrected as shown below:

In the Claims

At Column 11, Claim number 11, Line number 5, please add a "," after "diverging"

Signed and Sealed this
Twenty-first Day of April, 2020

Andrei Iancu
*Director of the United States Patent and Trademark Office*